(12) United States Patent  
Hatano

(10) Patent No.: US 9,636,002 B2
(45) Date of Patent: May 2, 2017

(54) ENDOSCOPE

(71) Applicant: OLYMPUS CORPORATION, Tokyo (JP)

(72) Inventor: Keisuke Hatano, Koganei (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/132,341

(22) Filed: Apr. 19, 2016

(65) Prior Publication Data

US 2016/0227984 A1 Aug. 11, 2016

Related U.S. Application Data

(63) Continuation of application No. PCT/JP2015/063306, filed on May 8, 2015.

(30) Foreign Application Priority Data

Sep. 16, 2014 (JP) ................. 2014-188042

(51) Int. Cl.
| | |
|---|---|
| *A61B 1/00* | (2006.01) |
| *A61B 1/005* | (2006.01) |
| *G02B 23/24* | (2006.01) |
| *A61B 1/05* | (2006.01) |
| *A61B 1/06* | (2006.01) |
| *A61B 1/04* | (2006.01) |

(52) U.S. Cl.
CPC ........ *A61B 1/0052* (2013.01); *A61B 1/00039* (2013.01); *A61B 1/0057* (2013.01); *A61B 1/00114* (2013.01); *A61B 1/05* (2013.01); *A61B 1/0676* (2013.01); *G02B 23/24* (2013.01)

(58) Field of Classification Search
CPC ..... A61B 1/005; A61B 1/0051; A61B 1/0052; A61B 1/0057; A61B 1/0676; A61B 1/00066
USPC .................................. 600/146–150
See application file for complete search history.

(56) References Cited

U.S. PATENT DOCUMENTS

2007/0149852 A1 6/2007 Noguchi et al.

FOREIGN PATENT DOCUMENTS

| | | |
|---|---|---|
| EP | 1787575 A1 | 5/2007 |
| JP | 2005-124632 A | 5/2005 |
| JP | 2006-055659 A | 3/2006 |
| JP | 2012-081010 A | 4/2012 |
| WO | WO 2006/028019 A1 | 3/2006 |

OTHER PUBLICATIONS

International Search Report dated Jun. 16, 2015 issued in PCT/JP2015/063306.

*Primary Examiner* — Timothy J Neal
(74) *Attorney, Agent, or Firm* — Scully, Scott, Murphy & Presser, P.C.

(57) ABSTRACT

An endoscope includes: an operation portion grasped by an operator; an insertion portion pivotable relative to the operation portion; a switch portion provided on the operation portion and switchable by a grasping hand of the operator; a pulling/relaxing member pulled and relaxed by back and forth movement in the operation portion based on switch operation of the switch portion; and a braking unit that includes a deformation portion deformed by the pulling and the relaxing of the pulling/relaxing member and that restrains or allows rotation of the insertion portion.

7 Claims, 9 Drawing Sheets

ENDOSCOPE

CROSS REFERENCE TO RELATED APPLICATION

This application is a continuation application of PCT/JP2015/063306 filed on May 8, 2015 and claims benefit of Japanese Application No. 2014-188042 filed in Japan on Sep. 16, 2014, the entire contents of which are incorporated herein by this reference.

BACKGROUND OF THE INVENTION

1. Field of the Invention

The present invention relates to an endoscope in which an insertion portion is pivotable relative to an operation portion.

2. Description of the Related Art

Conventionally, endoscopes including an insertion portion that can be inserted into a subject to observe the subject that cannot be directly viewed by an observer are proposed. Some of the endoscopes are provided with, for example, a rotation mechanism portion between the insertion portion and an operation portion, and a rotation operation handle of the rotation mechanism portion is rotated and operated to rotate the insertion portion.

More specifically, for example, Japanese Patent Application Laid-Open Publication No. 2005-124632 discloses a configuration including a rotation operation handle that rotates integrally with an insertion portion, and the rotation operation handle can be twisted to rotate the insertion portion relative to an operation portion. In the conventional endoscope, a stopper mechanism that restricts a rotation angle of the insertion portion relative to the operation portion is provided on a rotation mechanism portion.

SUMMARY OF THE INVENTION

An aspect of the present invention provides an endoscope including: an operation portion grasped by an operator; an insertion portion connected to a distal end side of the operation portion and pivotable relative to the operation portion; a switch portion provided on the operation portion and switchable by a hand of the operator grasping the operation portion; a pulling/relaxing member with one end connected to the switch portion, the pulling/relaxing member pulled and relaxed by back and forth movement in the operation portion based on switch operation of the switch portion; and a braking unit to which another end of the pulling/relaxing member is connected, the braking unit including a deformation portion deformed by the pulling and the relaxing of the pulling/relaxing member, the braking unit restraining or allowing rotation of the insertion portion.

According to the present invention described above, the rotation of the insertion portion relative to the operation portion can be restricted or allowed by the hand operation of the operator, and an endoscope with an improved operability can be provided.

DETAILED DESCRIPTION OF THE PREFERRED EMBODIMENT

Figure 1:
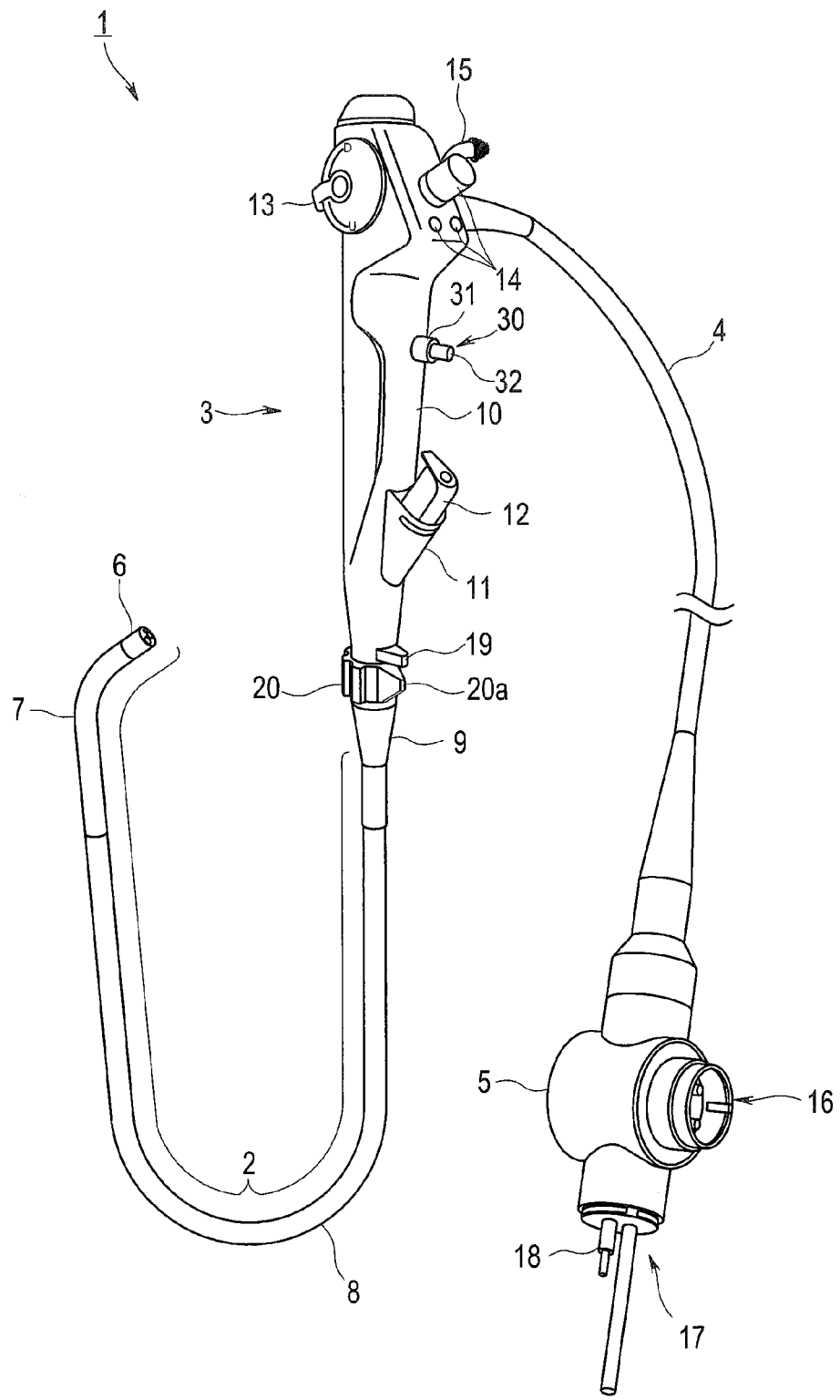
FIG. 1 is a diagram showing a configuration of an entire endoscope according to an aspect of the present invention.

Hereinafter, the present invention will be described with reference to the drawings. Note that scaling of each constituent element varies in each drawing used in the following description in order to illustrate each constituent element in a size that allows recognizing the constituent element on the drawing, and the present invention is not limited only to quantities of the constituent elements, shapes of the constituent elements, ratios of the sizes of the constituent elements, and relative positional relationships between respective constituent elements described in the drawings.

Figure 2:
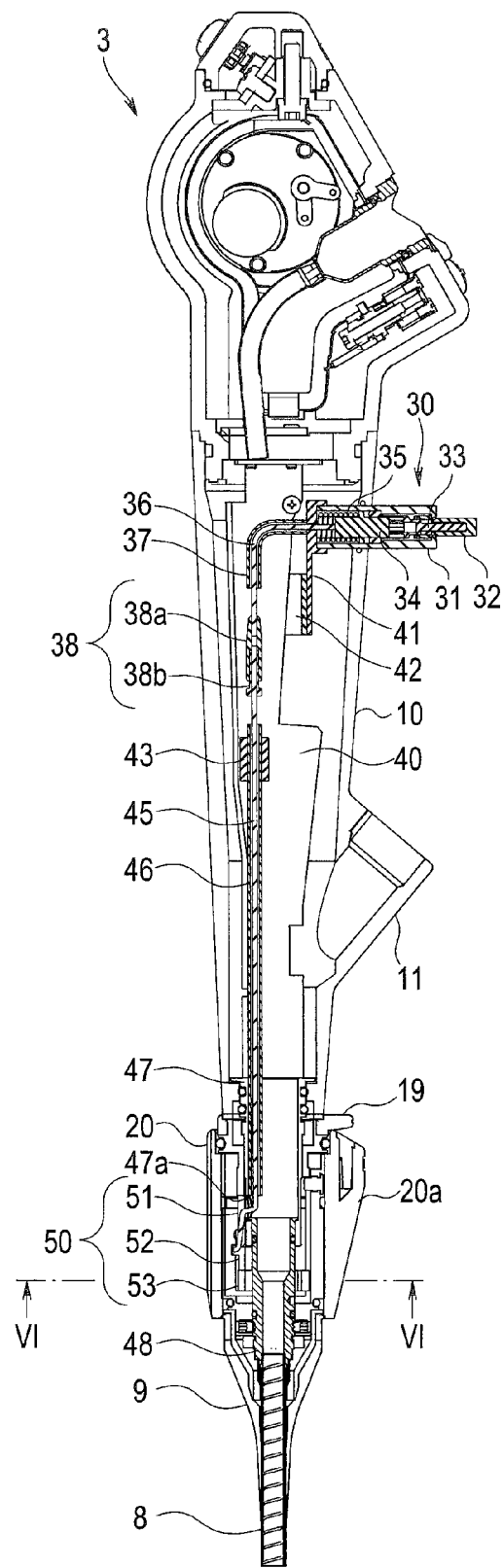
FIG. 2 is a partial cross-sectional view showing an internal configuration of an operation portion, mainly describing an insertion portion rotation restricting/allowing switch portion, an operation wire, and a braking unit according to the aspect of the present invention.
Figure 3:
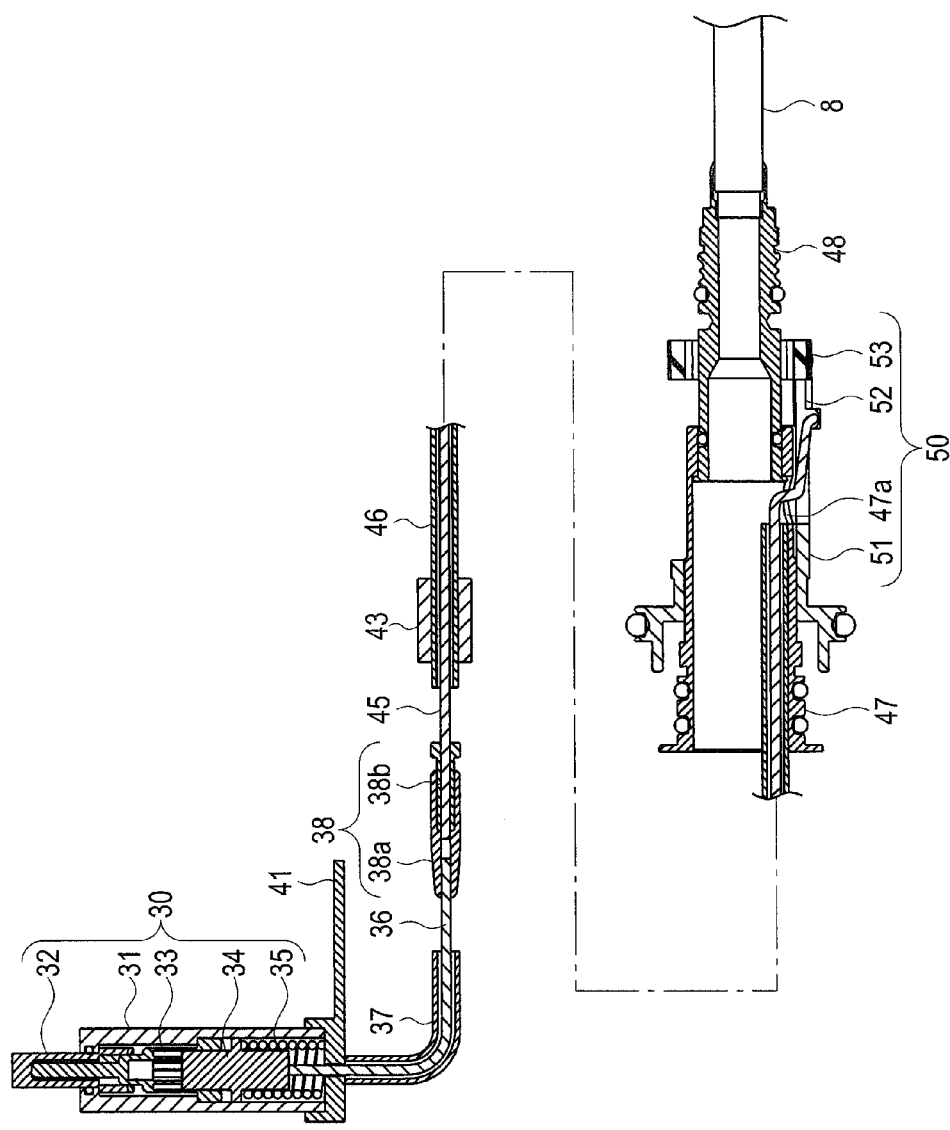
FIG. 3 is a cross-sectional view showing configurations of the insertion portion rotation restricting/allowing switch portion, the operation wire, and the braking unit according to the aspect of the present invention.
Figure 4:
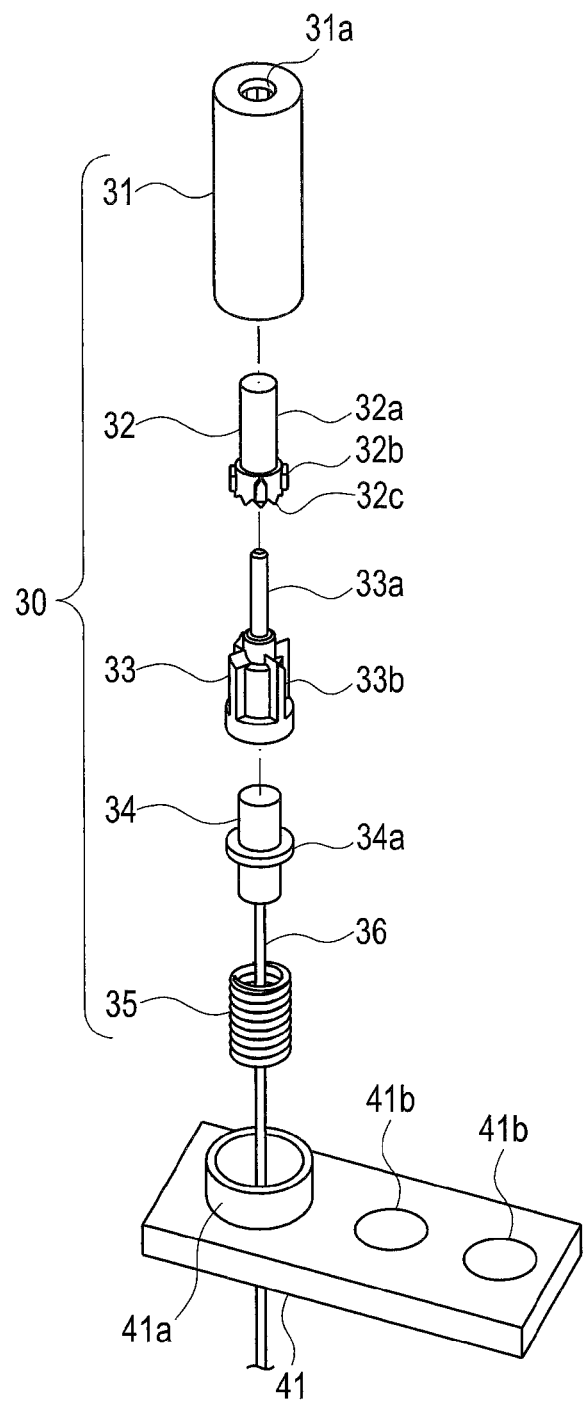
FIG. 4 is an exploded perspective view showing the configuration of the insertion portion rotation restricting/allowing switch portion according to the aspect of the present invention.
Figure 5:
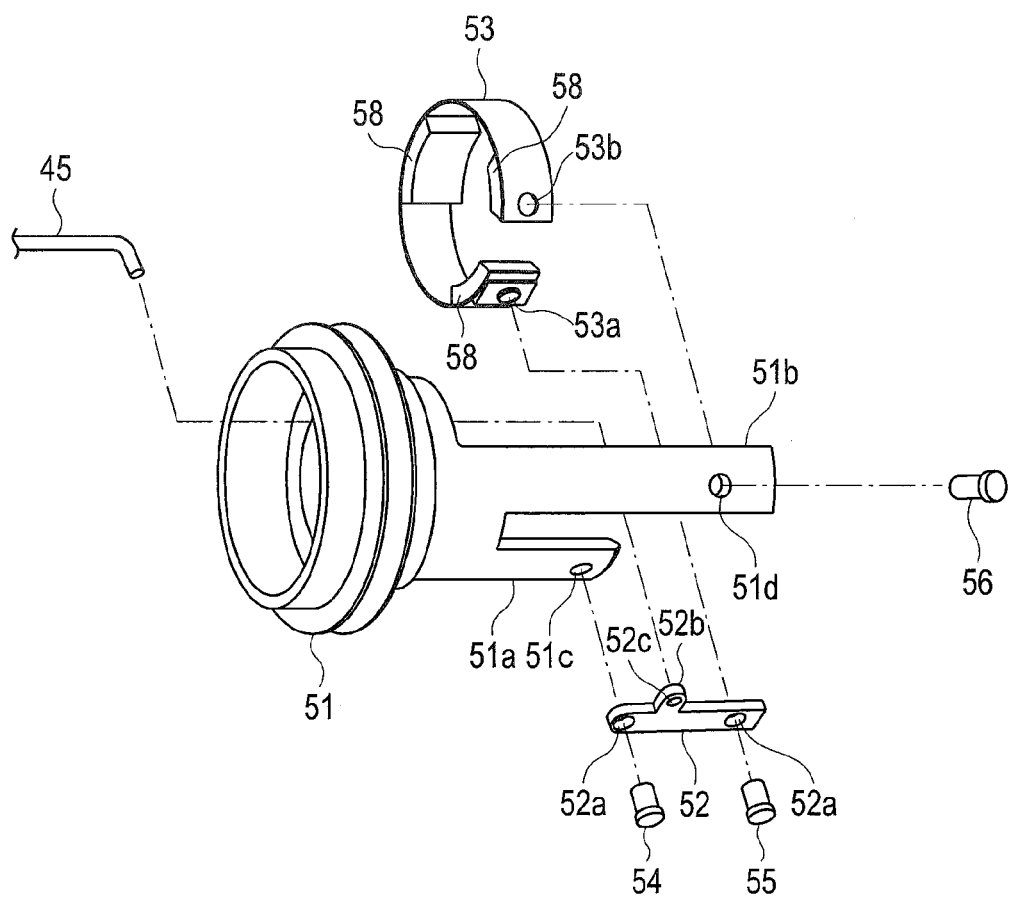
FIG. 5 is an exploded perspective view showing the configuration of the braking unit according to the aspect of the present invention.
Figure 6:
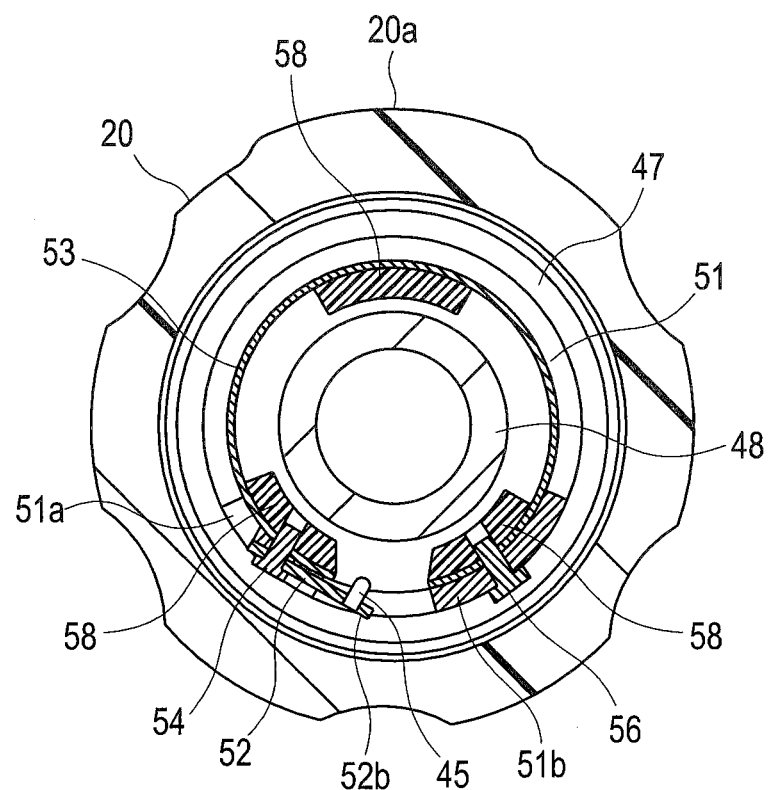
FIG. 6 is a cross-sectional view of a line VI-VI of FIG. 2 according to the aspect of the present invention.
Figure 7:
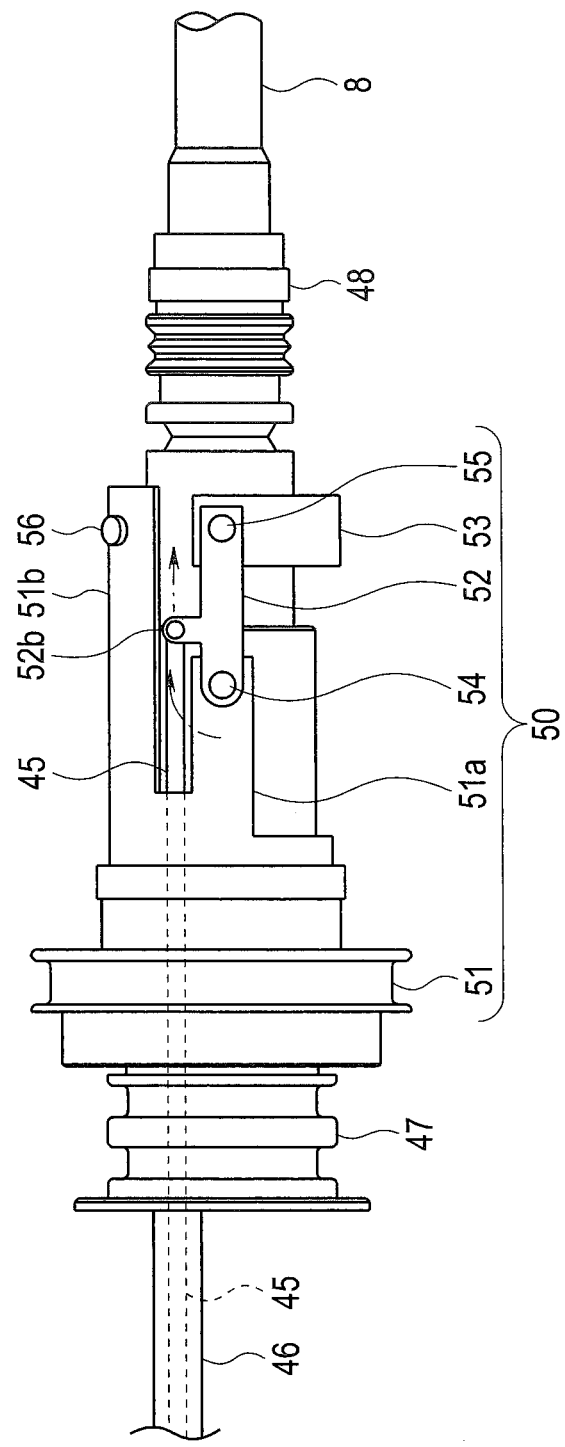
FIG. 7 is a plan view for describing the braking unit in a state in which rotation of an insertion portion relative to the operation portion is allowed according to the aspect of the present invention.
Figure 8:
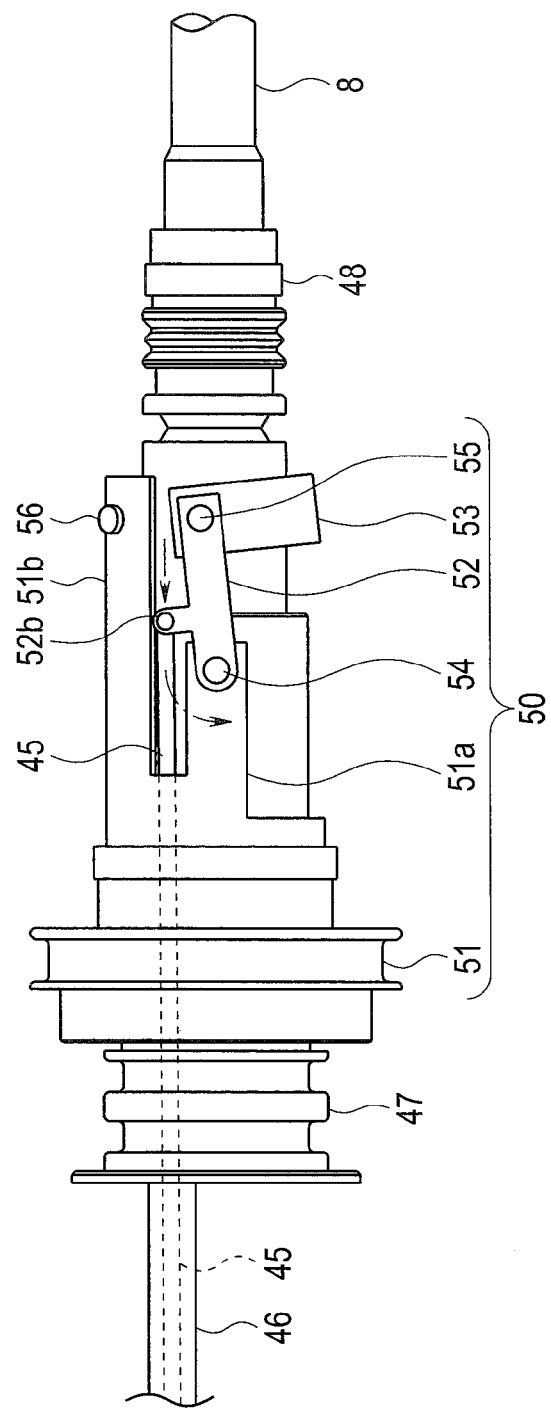
FIG. 8 is a plan view for describing the braking unit in a state in which the rotation of the insertion portion relative to the operation portion is restricted according to the aspect of the present invention.
Figure 9:
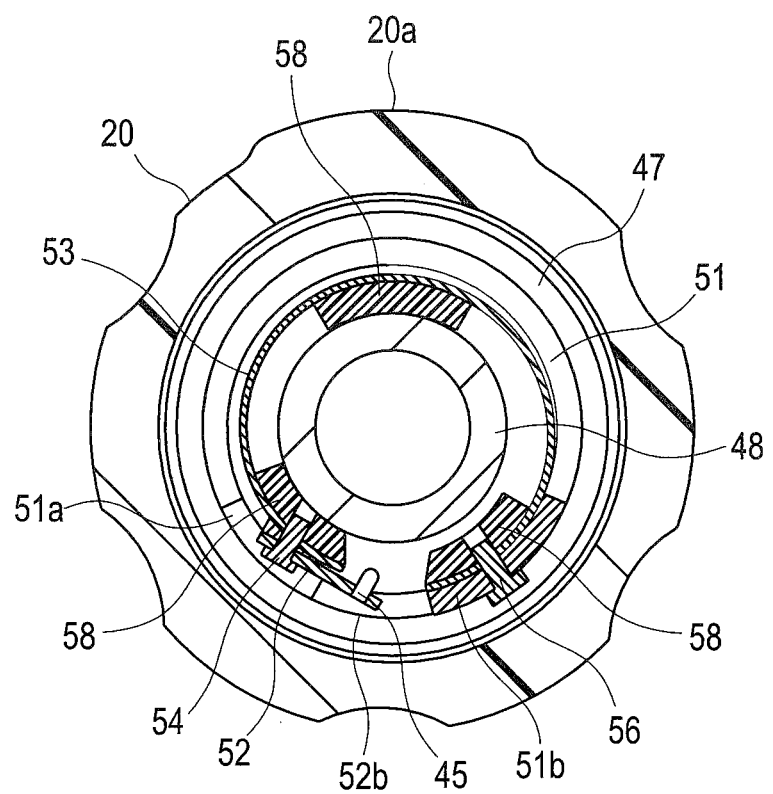
FIG. 9 is a cross-sectional view for describing the braking unit in the state in which the rotation of the insertion portion relative to the operation portion is restricted according to the aspect of the present invention.

FIGS. 1 to 9 are related to an endoscope according to an aspect of the present invention. FIG. 1 is a diagram showing a configuration of an entire endoscope. FIG. 2 is a partial cross-sectional view showing an internal configuration of an operation portion, mainly describing an insertion portion rotation restricting/allowing switch portion, an operation wire, and a braking unit. FIG. 3 is a cross-sectional view showing configurations of the insertion portion rotation restricting/allowing switch portion, the operation wire, and the braking unit. FIG. 4 is an exploded perspective view showing the configuration of the insertion portion rotation restricting/allowing switch portion. FIG. 5 is an exploded perspective view showing a configuration of the braking unit. FIG. 6 is a cross-sectional view of a line VI-VI of FIG. 2. FIG. 7 is a plan view for describing the braking unit in a state in which rotation of an insertion portion relative to the operation portion is allowed. FIG. 8 is a plan view for describing the braking unit in a state in which the rotation of the insertion portion relative to the operation portion is restricted. FIG. 9 is a cross-sectional view for describing the braking unit in the state in which the rotation of the insertion portion relative to the operation portion is restricted.

As shown in FIG. 1, an endoscope 1 of the present embodiment mainly includes: an insertion portion 2 formed in an elongated tubular shape; an operation portion 3 continuously connected to a proximal end of the insertion portion 2; a universal cord 4 that is an endoscope cable extending from the operation portion 3; an endoscope connector 5 installed on a distal end of the universal cord 4; and the like.

The insertion portion 2 is a tubular member with flexibility formed by continuously connecting a distal end portion 6, a bending portion 7, and a flexible tube portion 8 in order from a distal end side. Among these, the distal end portion 6 houses: an image pickup unit that is an image pickup apparatus described later including image pickup means inside; illumination means; and the like.

The bending portion 7 is a mechanism part configured to be able to actively bend in two vertical directions (UP-DOWN) by rotation operation of a bending lever 13 described later among operation members of the operation portion 3.

Note that the bending portion 7 is not limited to this type, and the bending portion 7 may be a type that can bend in four directions including horizontal directions in addition to the vertical directions (entire circumferential directions about an axis based on vertical and horizontal operations, UP-DOWN/RIGHT-LEFT).

The flexible tube portion 8 is a tubular member formed with flexibility so that the flexible tube portion 8 is passively flexible. In addition to a treatment instrument insertion channel described later, various signal lines described later that extend from the image pickup apparatus included in the distal end portion 6 and that are further extended inside of the universal cord 4 from the operation portion 3, a light guide described later for guiding illuminating light from a light source apparatus to emit the illuminating light from the distal end portion 6, and the like are inserted inside of the flexible tube portion 8 (here, these are not shown).

Note that the insertion portion 2 is provided to be pivotable about a longitudinal axis relative to the operation portion 3. More specifically, an insertion portion rotation dial 20 provided on a proximal end of a bend preventing portion 9 is rotated and operated, and the insertion portion 2 is rotated about the longitudinal axis relative to the operation portion 3, along with the bend preventing portion 9 covering a proximal end of the flexible tube portion 8 and connected to the flexible tube portion 8.

A handle convex portion 20a projects in an outer diameter direction from a part in a circumferential direction of the insertion portion rotation dial 20, and a position of the handle convex portion 20a is adjusted according to a position of a projecting indicator 19 provided on the operation portion 3 to position the insertion portion 2 at a neutral position relative to the operation portion 3.

Note that the neutral position is a position where a bending operation direction of the bending lever 13 that is a bending operation portion coincides with a bending direction of the bending portion 7. Another indicator (for example, a scale) for accurately adjusting the positions of the handle convex portion 20a and the indicator 19 may be further provided.

The operation portion 3 includes: a grasping portion 10 grasped by a hand when an operator uses the endoscope 1; operation means for operating various endoscope functions provided on an outer surface of the grasping portion 10; a treatment instrument insertion portion 11; a suction valve 15 that forms one of operation members 14 described later; and the like.

Examples of the operation means for operating various endoscope functions provided on the operation portion 3 include: the bending lever 13 for performing bending operation of the bending portion 7; the plurality of operation members 14 for performing air/water feeding operation, suction operation, and respective corresponding operations of the image pickup means, the illumination means, and the like; and an insertion portion rotation restricting/allowing switch portion 30 as a switch portion for restricting or allowing the rotation of the insertion portion 2 relative to the operation portion 3.

The treatment instrument insertion portion 11 is a constituent portion including a treatment instrument insertion port for inserting various treatment instruments (not shown) and connected to a treatment instrument insertion channel through a branch member inside of the operation portion 3. A forceps plug 12 that is a lid member for opening and closing the treatment instrument insertion port and that is detachable (exchangeable) relative to the treatment instrument insertion portion 11 is installed on the treatment instrument insertion portion 11.

Note that the insertion portion rotation restricting/allowing switch portion 30 provided on the operation portion 3 is arranged on a front surface part of the grasping portion 10 between the plurality of operation members 14 including the suction valve 15 provided on an upper side and the treatment instrument insertion portion 11 provided on a lower side.

The universal cord 4 is a composite cable through the inside of which various signal lines and the like inserted inside of the insertion portion 2 from the distal end portion 6 of the insertion portion 2, reaching the operation portion 3 and extending from the operation portion 3, the light guide of the light source apparatus (not shown) and an air/water feeding tube extending from an air/water feeding apparatus (not shown) are inserted.

The endoscope connector 5 includes: an electric connector portion 16 on a side surface portion, for connecting a signal cable for connection with a video processor (not shown) of an external device; a light source connector portion 17 for connecting a light guide bundle described later and an electric cable (not shown) for connection with the light source apparatus that is an external device; an air/water feeding plug 18 for connecting the air/water feeding tube (not shown) from the air/water feeding apparatus (not shown) of an external device; and the like.

Here, an internal configuration for restricting or allowing the rotation of the insertion portion 2 relative to the operation portion 3 will be described in detail. Note that a configuration that the insertion portion 2 is pivotable relative to the operation portion 3 is as in the conventional techniques and is well-known, and constituent elements and structures of the configuration will not be described.

The endoscope 1 of the present embodiment can switch the restriction or the allowing of the rotation of the insertion portion 2 relative to the operation portion 3 by pressing the insertion portion rotation restricting/allowing switch portion (hereinafter, simply called a switch portion) 30 provided on the grasping portion 10 of the operation portion 3.

As shown in FIGS. 2 and 3, the switch portion 30 is fixed by fitting or the like on a holding plate 41 fixed by a fixing member, such as a screw, on a base 42 provided on a frame 40 provided on the operation portion 3. Note that the switch portion 30 is installed to penetrate through a wall portion of the grasping portion 10 in a state that the switch portion 30 is held in a watertight manner by an O-shaped ring.

Note that the switch portion 30 is arranged on a substantially straight line connecting the suction valve 15 and the treatment instrument insertion portion 11 and arranged on an upper side in a bending direction between the suction valve 15 and the treatment instrument insertion portion 11. Therefore, the endoscope 1 allows effortless operation of the switch portion 30 by a hand of a user grasping the operation portion 3, regardless of whether the operation portion 3 is grasped by a left hand or a right hand.

From the switch portion 30, one end as a proximal end of a first wire 36 that is an operation wire of a pulling/relaxing member inserted into an L-shaped first wire guard 37 is connected. The other end as a distal end of the first wire 36 is connected to a turnbuckle 38 that is a connection metal fitting. Note that the first wire guard 37 may be a coil pipe or may be a rigid tube body.

In the turnbuckle 38 here, a female retaining screw metal fitting 38a is screwed, and a male retaining screw metal fitting 38b is screwed to the female retaining screw metal fitting 38a. According to degrees of screwing of the female retaining screw metal fitting 38a and the male retaining screw metal fitting 38b, the turnbuckle 38 can adjust tensile force of the first wire 36 and a second wire 45 connected to both ends described later that is an operation wire of the pulling/relaxing member.

Here, the other end as a distal end side of the first wire 36 is connected by a swage or the like to the female retaining screw metal fitting 38a, and one end as a proximal end of the second wire 45 is connected by a swage or the like to the male retaining screw metal fitting.

The second wire 45 is also inserted into a second wire guard 46 that is a coil pipe or a rigid tube. A proximal end portion of the second wire guard 46 is inserted into and fixed to a wire guard receiving portion 43 provided on the frame 40.

Note that the first wire guard 37 and the second wire guard 46 serve as protection members that protect the first wire 36 and the second wire 45 inserted into the first wire guard 37 and the second wire guard 46, respectively, and that protect other constituent components from back and forth movement of the first wire 36 and the second wire 45. The first wire guard 37 and the second wire guard 46 further prevent rough behaviors of the first wire 36 and the second wire 45 moving back and forth inside.

By the way, a plurality of O-shaped rings are provided to fit and fix a substantially cylindrical fixing pipe sleeve 47 in a watertight state to a distal end of the grasping portion 10 of the operation portion 3. Through an opening portion 47a formed on the fixing pipe sleeve 47, the second wire 45 is extended to an inside part of the insertion portion rotation dial 20 from inside of the grasping portion 10.

The other end of the second wire 45 that is a distal end extended inside of the insertion portion rotation dial 20 is connected to a braking unit 50 described later.

Note that an O-shaped ring is provided on the fixing pipe sleeve 47 as in conventional configurations, and a back pipe sleeve 48 is pivotably installed in a state that the back pipe sleeve 48 is held in a watertight manner. A proximal end of the flexible tube portion 8 of the insertion portion 2 is connected and fixed to the back pipe sleeve 48, and the insertion portion rotation dial 20 and the bend preventing portion 9 are fixed. In this way, the insertion portion 2 is pivotable about the axis relative to the operation portion 3.

Next, the configuration of the switch portion 30 will be described in detail.

As shown in FIG. 4, the switch portion 30 is a so-called knock type extending switch mechanism portion and includes a substantially cylindrical exterior portion 31, a knock rod 32, a rotor 33, a substantially columnar spring retainer 34, and a coil spring 35.

The exterior portion 31 includes an opening portion 31a on one end, and a groove not shown is formed on an inner circumferential surface. The knock rod 32 is housed in the exterior portion 31 such that a rod-shaped operation rod body 32a protrudes from the opening portion 31a of the exterior portion 31 and is operated to project and retract relative to the exterior portion 31.

Note that an O-shaped ring is provided between the exterior portion 31 and the knock rod 32, and the switch portion 30 is held in the watertight state even when the knock rod 32 is operated to project and retract relative to the exterior portion 31.

The knock rod 32 also includes, on an outer circumferential portion, a plurality of projection portions 32b that linearly move along a groove (not shown) of the exterior portion 31, and a concave and convex portion 32c is formed on a surface on the opposite side of the operation rod body 32a.

The rotor 33 includes a rod body 33a inserted into and rotated and held in the knock rod 32, and a cam 33b that comes in contact with the concave and convex portion 32c to rotate is formed on an outer circumferential portion according to the projection and recession of the knock rod 32. That is, the cam 33b comes in contact with the concave and convex portion 32c of the knock rod 32, and the rotor 33 is rotated about the axis.

The first wire 36 that is an operation wire is connected to the spring retainer 34, and an outward flange 34a is formed in the middle of an outer circumferential portion. The outward flange 34a comes in contact with one end of the coil spring 35 and receives urging force on one side.

In the switch portion 30 with the configuration, the rotor 33 rotates in a predetermined direction when the operator presses the knock rod 32, and the cam 33b is hooked to a convex portion including a V-shaped end surface not shown formed on an inner surface of the exterior portion 31 according to the rotation position.

In this case, the rotor 33 presses the spring retainer 34 and is restrained while compressing the coil spring 35. As a result, part of the knock rod 32 is retracted into the exterior portion 31 in the switch portion 30, and the first wire 36 connected to the spring retainer 34 is relaxed.

From this state, when the operator presses again the knock rod 32 in which part of the knock rod 32 is retracted into the exterior portion 31 in the switch portion 30, the rotor 33 further rotates in a predetermined direction, and the cam 33b comes outs from the V-shaped end surface (not shown) formed on the convex portion of the exterior portion 31.

In this case, the rotor 33 is returned by receiving the urging force of the coil spring 35 through the spring retainer 34, and the knock rod 32 projects relative to the exterior portion 31. As a result, the first wire 36 connected to the spring retainer 34 is pulled.

That is, the switch portion 30 here is a knock type extending switch mechanism portion adopted in a knock type ballpoint pen and the like. Note that in the switch portion 30, an end portion of the exterior portion 31 is fitted and fixed to a cylindrical fitting portion 41a formed on the holding plate 41. Two screw holes 41b for fixation to the base 42 (see FIG. 2) are formed on the holding plate 41.

Next, the configuration of the braking unit 50 will be described in detail.

As shown in FIGS. 5 and 6, the braking unit 50 mainly includes: a substantially annular support pipe sleeve 51; a T-shaped link member 52; and a leaf spring 53 that is a deformation portion with a C-shaped cross section.

The support pipe sleeve 51 is fitted outside and fixed to the fixing pipe sleeve 47 (see FIG. 3), and a short arm portion 51a and a long arm portion 51b are extended on a distal end side in a longitudinal direction (direction orthogonal to an annular outer diameter direction).

Note that although described in detail later, one end of the link member 52 is pivotably connected to the short arm portion 51a, and the leaf spring 53 as an elastic member is connected to the long arm portion 51b.

Screw holes 52a are formed on both ends of the link member 52, and screws 54 and 55 are inserted into the screw holes 52a. An end portion of the second wire 45 is inserted into a hole portion 52c of a convex portion 52b projecting from the middle and is fixed by brazing, soldering, and the like.

The screw 54 is inserted into the screw hole 52a on one end that is a proximal end side, and the screw 54 is screwed to a screw hole 51c of the short arm portion 51a of the support pipe sleeve 51 to pivotably install the link member 52 relative to the short arm portion 51a.

In this case, the link member 52 is pivotably installed relative to the short arm portion 51a such that the convex portion 52b connected with the second wire 45 is positioned between the short arm portion 51a and the long arm portion 51b of the support pipe sleeve 51. Note that the second wire 45 is inserted into an annular portion of the support pipe sleeve 51 from between the short arm portion 51a and the long arm portion 51b of the support pipe sleeve 51.

Furthermore, in the link member 52, the screw 55 is inserted into the screw hole 52a on the other end that is a distal end side, and the screw 55 is screwed to a screw hole 53a formed on one end of the leaf spring 53 to fix the leaf spring 53.

Three brake shoes 58 as braking members are provided at predetermined intervals on an inner surface of the leaf spring 53, and a screw 56 inserted into a screw hole 51d of the long arm portion 51b of the support pipe sleeve 51 is screwed to a screw hole 53b formed on the other end. That is, one end of the leaf spring 53 with the C-shaped cross section is connected and fixed to the link member 52, and the other end is connected and fixed to the long arm portion 51b of the support pipe sleeve 51.

Note that the three brake shoes 58 are fixed by an adhesive or the like to both end parts and in the middle of the leaf spring 53. Two brake shoes 58 provided on both end parts of the leaf spring 53 are also screwed to the screws 55 and 56 fixed to the link member 52 or the long arm portion 51b of the support pipe sleeve 51. Note that the three brake shoes 58 are arranged to face an outer circumferential face of the back pipe sleeve 48 connected with the flexible tube portion 8 of the insertion portion 2.

The endoscope 1 of the present embodiment with the configuration can restrict or allow the rotation of the insertion portion 2 relative to the operation portion 3 by pressing operation of the switch portion 30 provided on the grasping portion 10 of the operation portion 3.

More specifically, when the operator performs predetermined pressing operation of the knock rod 32 of the switch portion 30, and the first wire 36 is in the relaxed state in the endoscope 1, the second wire 45 connected to the first wire 36 through the turnbuckle 38 is also in the relaxed state.

In this case, the link member 52 of the braking unit 50 is parallel to a longitudinal direction of the support pipe sleeve 51 as shown in FIG. 7, and the leaf spring 53 with the C-shaped cross section is in a natural state.

In this state, the three brake shoes 58 provided on the leaf spring 53 are separated from and face an outer circumferential portion of the back pipe sleeve 48 as shown in FIG. 6, and the back pipe sleeve 48 is pivotable relative to the fixing pipe sleeve 47.

As a result, the insertion portion 2 connected to the back pipe sleeve 48 is pivotable relative to the operation portion 3. That is, this state is a state in which the rotation of the insertion portion 2 relative to the operation portion 3 in the endoscope 1 is allowed (freed).

On the other hand, when the operator performs predetermined pressing operation of the knock rod 32 of the switch portion 30 in the endoscope 1 from this state, the mechanism of the switch portion 30 pulls the first wire 36 to the proximal end side and also pulls the second wire 45 connected to the first wire 36 through the turnbuckle 38.

In this case, as shown in FIG. 8, the convex portion 52b of the link member 52 of the braking unit 50 is pulled by the second wire 45, and the link member 52 is rotated from the state parallel to the longitudinal direction of the support pipe sleeve 51, the screw 54 rotated and supported by the short arm portion 51a serving as a rotation shaft.

The leaf spring 53 connected to the end portion (other end) on the distal end side is twisted and pulled by the link member 52.

As a result, the leaf spring 53 is distorted in an inner diameter direction, and a diameter is reduced. As shown in FIG. 9, the three brake shoes 58 are pressed against the leaf spring 53 so as to press an outer circumferential portion of the back pipe sleeve 48 that is a member to be braked here, and the rotation of the back pipe sleeve 48 relative to the fixing pipe sleeve 47 is braked. That is, the state is a state in which the rotation of the insertion portion 2 relative to the operation portion 3 in the endoscope 1 is restricted (locked).

Note that the operator can perform again the pressing operation of the switch portion 30 provided on the grasping portion 10 of the operation portion 3 to thereby allow the rotation of the insertion portion 2 relative to the operation portion 3 from the restricted state.

In this way, the switch portion 30 is provided on the grasping portion 10 of the operation portion 3 in the endoscope 1 of the present embodiment, and the rotation of the insertion portion 2 relative to the operation portion 3 can be restricted or allowed by hand operation by the operator grasping the grasping portion 10. Operability is significantly improved in the endoscope 1.

Particularly, during endoscopy, the operator can restrict the rotation of the insertion portion 2 just by the operation of the switch portion 30 by the hand grasping the grasping portion 10 of the operation portion 3, from the state in which the insertion portion 2 is adjusted to a desired rotation position relative to the operation portion 3. As a result, the endoscope 1 can prevent deviation of the desired rotation position of the insertion portion 2 set by the operator.

According to the description, the endoscope 1 of the present embodiment can easily switch the restriction or the allowing of the rotation of the insertion portion 2 relative to the operation portion 3 by the hand operation of the operator, and the operability can be improved.

Furthermore, in the endoscope 1 of the present embodiment, the first wire 36 or the second wire 45 inserted into the first wire guard 37 or the second wire guard 46 is pulled and relaxed to drive the braking unit 50 by the operation of the switch portion 30.

Therefore, when the rotation of the insertion portion 2 relative to the operation portion 3 is restricted or allowed in the endoscope 1, the first wire 36 or the second wire 45 does not damage other internal components, such as a light guide bundle, a bending operation wire, and an image pickup cable, installed in the operation portion 3.

The invention described in the embodiment described above is not limited to the embodiment and modifications, and various other modifications can be carried out in an execution phase without departing from the scope of the invention. Furthermore, the embodiment includes inventions of various phases, and various inventions can be extracted based on appropriate combinations of a plurality of disclosed constituent conditions.

For example, when the problem to be solved by the invention can be solved, and the advantageous effects described in the advantageous effects of the invention can be obtained even if some of the constituent conditions out of all the constituent conditions illustrated in the embodiment are eliminated, the configuration after the elimination of the constituent conditions can be extracted as an invention.

What is claimed is:

1. An endoscope comprising:
   an operation portion grasped by an operator;
   an insertion portion connected to a distal end side of the operation portion and pivotable relative to the operation portion;
   a switch provided on the operation portion and switchable by a hand of the operator grasping the operation portion;
   a pulling/relaxing member including a first end and a second end, the first end being connected to the switch, the pulling/relaxing member being pulled and relaxed by a switch operation of the switch; and
   a brake to which the second end of the pulling/relaxing member is connected, the brake comprising a movable portion to be moved by the pulling and the relaxing of the pulling/relaxing member, the brake restraining or allowing rotation of the insertion portion.

2. The endoscope according to claim 1, wherein
   the movable portion is moved by deformation by the pulling of the pulling/relaxing member, and
   the brake restrains the rotation of the insertion portion.

3. The endoscope according to claim 2, wherein the movable portion is disposed around an outer circumferential portion of a member to be braked connected to a proximal end of the insertion portion and the movable portion comprises an elastic member with a C-shaped cross section in which a diameter is reduced by the pulling of the pulling/relaxing member.

4. The endoscope according to claim 3, wherein the movable portion comprises a braking surface provided on an inner surface of the elastic member, when the diameter of the C-shaped cross section is reduced, the braking surface presses the outer circumferential portion of the member to be braked to brake the rotation of the insertion portion.

5. The endoscope according to claim 1, wherein the switch is installed between a plurality of operation members provided on the operation portion and a treatment instrument insertion portion provided distally to the plurality of operation members on the operation portion.

6. The endoscope according to claim 5, wherein the switch is arranged on a substantially straight line connecting a suction valve that is one of the plurality of operation members and the treatment instrument insertion portion.

7. The endoscope according to claim 1, wherein a protection member to which the pulling/relaxing member is inserted is included in the operation portion.

* * * * *